United States Patent
Guoliang et al.

(10) Patent No.: US 6,411,905 B1
(45) Date of Patent: Jun. 25, 2002

(54) METHOD AND APPARATUS FOR ESTIMATING ODOR CONCENTRATION USING AN ELECTRONIC NOSE

(75) Inventors: Qu Guoliang; John R. Feddes, both of Edmonton; Richard N. Coleman, Vergreville; William W. Armstrong; Jerry J. Leonard, both of Edmonton, all of (CA)

(73) Assignees: The Governors of the University of Alberta; Alberta Research Council Inc., both of Edmonton (CA)

( * ) Notice: Subject to any disclaimer, the term of this patent is extended or adjusted under 35 U.S.C. 154(b) by 149 days.

(21) Appl. No.: 09/618,479

(22) Filed: Jul. 18, 2000

(51) Int. Cl.$^7$ .................................................. G01N 1/22
(52) U.S. Cl. ........................ 702/23; 73/23.34; 73/31.05; 73/31.06
(58) Field of Search ................. 702/23, 165, FOR 124; 364/506, 551.01; 73/23.34

(56) References Cited

U.S. PATENT DOCUMENTS

| | | | |
|---|---|---|---|
| 4,563,893 A | | 1/1986 | Tanyolac et al. |
| 5,177,994 A | | 1/1993 | Moriizumi et al. |
| 5,253,329 A | | 10/1993 | Villarreal et al. |
| 5,571,401 A | | 11/1996 | Lewis et al. |
| 5,623,212 A | | 4/1997 | Yamanaka |
| 5,627,307 A | | 5/1997 | Hayashi |
| 5,675,070 A | * | 10/1997 | Gelperin ..................... 73/23.34 |
| 5,766,551 A | | 6/1998 | Dispirito et al. |

(List continued on next page.)

OTHER PUBLICATIONS

Krishna C. Persaud et al. Assessment of Conducting Polymer Odour Sensor for Agricultural Malodour Measurements—Oxford University Press.

P.J. Hobbs et al. Assessment of Odours From Livestock Wastes by a Photoionization Detector, an Electronic Nose, Olfactometry and Gas Chromatography–Mass Spectrometry Jagric. Engng Res. (1995) 60, 137–144 1995 Silcoe Research Institute.

T. H. Misselbrook et al. Use of an Electronic Nose to Measure Odour Concentration Following Application of Cattle Slurry to Grassland, J. agric. Engng Res. (1997) 66, 213–220 1997 Silsoe Research Institute.

*Primary Examiner*—Marc S. Hoff
*Assistant Examiner*—Felix Suarez

(57) ABSTRACT

A system and method for obtaining an estimate of the concentration of an odor in an air sample from data obtained by evaluating the sample with a sensor-array type electronic nose. Principal components analysis is applied to a set of air sample data including sensor-array data obtained from evaluating the air sample with the sensor-array type electronic nose and measurements of the humidity of the air sample and clean reference air used by the electronic nose to obtain a predetermined number of principal components of the air sample data. The principal components obtained from the air sample are used as inputs to a neural network to obtain as output an estimate of the concentration of the odor in the air sample. The neural network uses parameters obtained by using an olfactometer to obtain discrete measurements of odor concentration from each of a plurality of calibration samples of air containing the odor, using the sensor-array type electronic nose to obtain a discrete set of calibration data from each of the calibration samples, each set including sensor-array data and measurements of the humidity of the calibration sample and the clean reference air used by the electronic nose, applying principal components analysis to each set of calibration data to obtain a discrete set of the predetermined number of principal components, and training a neural network using the sets of principal components as input data and the corresponding measured odor concentrations as expected output to obtain the parameters of a trained neural network.

8 Claims, 4 Drawing Sheets

U.S. PATENT DOCUMENTS

| | | |
|---|---|---|
| 5,788,833 A | 8/1998 | Lewis et al. |
| 5,801,297 A * | 9/1998 | Mifsud et al. ............. 73/23.34 |
| 5,911,872 A | 6/1999 | Lewis et al. |
| 5,918,257 A * | 6/1999 | Mifsud et al. ............. 73/23.34 |
| 5,946,640 A | 8/1999 | Goodacre et al. |
| 6,006,583 A | 12/1999 | Hayashi |
| 6,017,440 A | 1/2000 | Lewis et al. |

* cited by examiner

METHOD AND APPARATUS FOR ESTIMATING ODOR CONCENTRATION USING AN ELECTRONIC NOSE

FIELD

The present invention relates to a method and apparatus for obtaining useful measurements from an electronic nose and, more particularly, to a method and system for obtaining an estimate of odor concentration from data obtained from a sensor-array type electronic nose.

BACKGROUND

Odor concentration is measured by determining the dilution factor required to reach the human detection threshold. The odor concentration is then expressed in terms of multiples of the detection threshold. The detection threshold is defined as the dilution factor at which the sample has a 50% probability of being detected under the conditions of the test.

Odor concentration is conventionally measured by an instrument called an olfactometer, the use of which requires a panel of persons who have been selected and trained following standard methods (see ASTM Special Technical Publication 758: Guidelines for Selection and Training of Sensory Panel Members; CEN/TC264/WG2 1998: Draft European CEN Standard: Air-quality-determination of odour concentration by dynamic olfactometry). Using an olfactometer with a human panel is presently the most precise method for quantifying odors. However, the use of human panels to evaluate odor samples is labor intensive, time consuming, prone to errors, and cannot be used a remote sites. The measurement accuracy obtainable with an olfactometer is dependent upon both the olfactometer and the human panel. Huge variations in olfactory sensitivity are found, even among "normal people". There is a clear need for a less labor-intensive, mobile way to measure odor concentration that is at least as accurate as an olfactometer.

Electronic noses, such as the AromaScan™ electronic nose (commercially available from AromaScan Inc., 14 Clinton Drive, Hollis, N. H.), use conducting polymer sensor arrays to mimic the human olfactory system in the classification, discrimination, and recognition of chemical patterns occurring in odor samples. However, electronic noses have not been successfully used to make quantitative measurements of odor concentration as defined above, but have been used to make measurements of patterns of odor mixtures and of physical parameters such as partial pressure and mole fraction. While such measurements are useful in quality control in food, beverage, perfume, and cosmetic industries and in detecting dangerous concentrations of pollutants, they are not useful in determining whether an odor will be detected by humans and quantitatively how offensive an odor will be to humans.

An electronic nose works by measuring the changes in electrical resistance of the sensors when exposed to an odor. The AromaScan™ electronic nose, for example, has 32 different sensors in its array, each of which will in general exhibit a specific change in electrical resistance when exposed to air containing an odor. The selective interaction of odors with the sensors produces a pattern of resistance changes for each odor. If an odor is composed of many chemicals, the pattern will be the result of their combined interactions with all of the sensors in the array. It has also been found that the response of the array to varying concentrations of the same odor is non-linear.

There have been some suggestions in the research literature that an electronic nose could be used for measurement of odor concentration. For example, see Hobbs et al. (Assessment of odours from livestock wastes by a photo-ionisation detector, an electronic nose, olfactometry and gas-chromatography-mass spectrometry. J. Agric.Engng Res. (1995) 60, 137–144) in which an evaluation of the response of an electronic nose against odor concentration measurement by an olfactometer is described. The electronic nose used was not sufficiently sensitive to be used to measure concentration, but could distinguish types of odors at high concentrations. There was no discussion of how odor concentration might be esitmated from the sensor-array response as there was no range of odor concentration over which the sensor array would respond.

By the time of a paper by Persaud et al. (Assessment of conductng polymer odour sensors for agricultural malodour measurements. Chemical Senses 1996, 21, 495–505), sensor array construction appeared to have improved as in that paper the response of a sensor array to the odor of a number of components of pig slurry was observed over a range of concentrations. It was observed that the normalized responses of the sensors to the various components changed with concentration. Reduction of the number of dimensions in the data was used in the analysis. The effect of humidity was also observed, but a correlation between sensor sensitivity and human sensitivity was not determined, nor was a method suggested for doing so. However, use of conducting polymer sensor arrays was found suitable for odor concentration estimation.

Misselbrook et al. (Use of an Electronic Nose to Measure Odour Concentration Following Application of Cattle Slurry to Grassland J. Agric.Engng Res. (1997) 66, 213–220) describes work done with two types of electronic nose, one of which was an AromaScan™ electronic nose. The paper describes calculation of normalized sensor responses and the application of principal components analysis to sets of normalized sensor responses at different odor concentrations and to sets of actual sensor readings. The analysis reported in the paper indicated that there was a definite concentration effect using in sets of actual sensor readings, although no regression (linear or otherwise) was done. The paper suggests that "using pretrained knowledge about the relationship between sensor response (either average sensor response or actual sensor response pattern) and odor concentration" for a particular odor type, it should be possible for an electronic nose to estimate a value for the odor concentration of a sample with which it is presented. This paper does not describe or suggest how to use neural networks to find a relationship between sensor response and odor concentration.

The only patents known to the inventors in which neural networks are mentioned in connection with measurement of odors by sensor arrays are those in the family of U.S. patents assigned to the California Institute of Technology (U.S. Pat. Nos. 5,571,401; 5,698,089; 5,778,833; 5,891,398; 5,911,872; 5,951,846; 5,959,191; 6,010,616; and 6,017,440). However, these patents do not describe at all how to use a neural network to obtain an estimate of odor concentration. They do disclose use of a sensor array and the use of principal components analysis to reduce the dimensionality of the data obtained from a sensor array. However, they do not describe or suggest the use of a neural network or any other non-linear fitting technique to convert preprocessed sensor array data to an estimate of odor concentration. In fact, no reference is made at all to estimating odor concentration or providing an electronic substitute for an olfactometer. The fitting that they describe is a multi-linear least squares fitting to obtain physical parameters such as partial pressure and mole fraction, not odor concentration. In particular, they describe using a multi-linear least squares fit through the first three principal components to the determine mole fractions of components in a mixture of gases.

No other patents known to the inventors describe a method or an apparatus that could be used for estimating odor concentration by a single direct measurement by a sensor array, although two patents (Hayashi, U.S. Pat. Nos. 5,627,307 and 6,006,583) describe apparatus for measuring odor concentration by repeated dilution down to a level at which a sensor produces a voltage known to indicate that the detection threshold for humans has been reached. Neural networks have been described in conjunction with devices for identification or discrimination of odors in several patents, but none suggested use in conjunction with odor concentration estimation.

There is thus a need to develop a method and apparatus for using an electronic nose to estimate odor concentration.

SUMMARY

In one embodiment of the inventive apparatus, a processor component applies principal components analysis to a set of air sample data including sensor-array data obtained from evaluating an air sample containing an unknown concentration of an odor with the sensor-array type electronic nose and measurements of the humidity of the air sample and clean reference air used by the electronic nose to obtain a predetermined number of principal components of the air sample data. The principal components of the air sample data are then processed by a neural network component to obtain as output an estimate of the concentration of the odor in the air sample. The neural network uses parameters obtained by:

(1) using an olfactometer to obtain discrete measurements of odor concentration from each of a plurality of calibration samples of air containing the odor.

(2) using the sensor-array type electronic nose to obtain a discrete set of calibration data from each of the calibration samples, each set including sensor-array data and measurements of the humidity of the calibration sample and the clean reference air used by the electronic nose, (3) applying principal components analysis to each set of calibration data to obtain a discrete set of the predetermined number of principal components, and (4) training a neural network using the sets of principal components as input data and the corresponding measured odor concentrations as expected output to obtain the parameters of a trained neural network.

More generally, any data processing that reducing noise in the air sample data and calibration data and, where possible, the reduces the dimensionality of that data may be used in place of principal components analysis to train the neural network.

Non-linear transformations based upon non-linear regression of the calibration data and measured odor concentrations may be used in place of a neural network.

DETAILED DESCRIPTION

Figure 1:
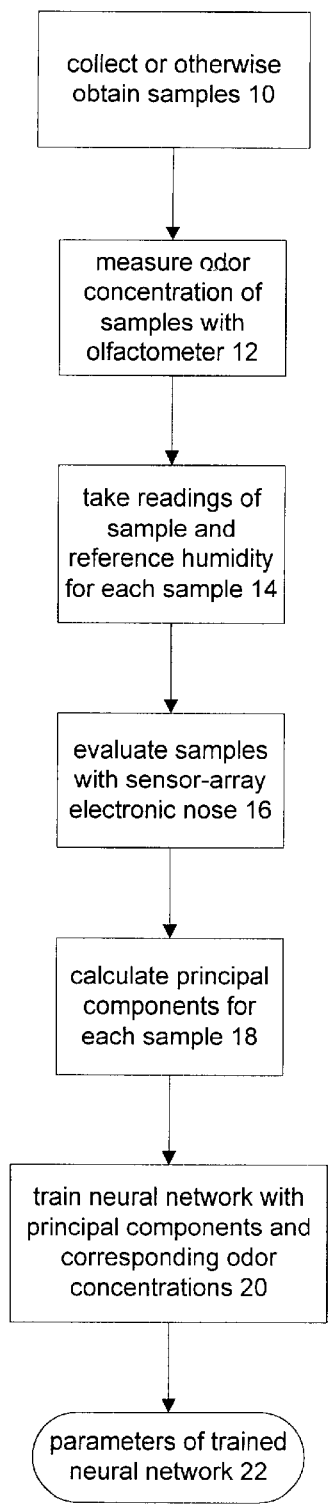
FIG. 1 is a schematic data flow diagram that illustrates the training of a neural network to estimate odor concentration.

The apparent non-linearity of variations in the pattern of resistances of the sensor array elements in an electronic nose such as the AromaScan™ electronic nose as a result of changes in concentration of an odor may be used to obtain quantitative estimates of the concentration of that odor in the manner described below. By varying non-linearly, we mean that the normalized patterns of sensor-array readings of an electronic nose taken of the same odor at two different dilutions are not the same.

The AromaScan™ electronic nose was used in developing the embodiment of the invention described below, but other sensor-array type electronic noses may be used as well. The AromaScan™ electronic nose uses conducting polymer sensors. Some of the other sensor types that are used in sensor-array type electronic noses to which the invention may be applied are metal oxide semi-conducting sensors, quartz crystal microbalance sensors, surface acoustic wave sensors, and hybrids of those types. Essentially any electronic nose that provides a plurality of measurements the pattern of which varies non-linearly with odor concentration may be used in conjunction with the inventive method.

The inventive method may be embodied in apparatus whose detailed design is within the skill of those of ordinary skill in the art. The following description does not therefore provide detailed explanations of the required electronics or software needed to practice the invention.

A typical use of the inventive method may be in a portable apparatus for estimating odor concentration in the vicinity of feed lots. In developing the inventive method, eight odor samples were obtained respectively from the ventilation exhaust stream of swine housing and slurry processing buildings at four farms. Multiple measurements of the samples were taken using both a conventional olfactometer and an electronic nose and a useful relationship found between the pattern of sensor array resistance changes (from a reference air sample) and the odor concentration measured by the olfactometer. The method used in finding that relationship is believed to be applicable generally to sensor-array electronic noses and may be used to construct apparatus for estimating of odor concentration.

The challenge in finding a useful relationship was that a typical electronic nose such as the AromaScan™ electronic nose produces a plurality of sensor readings for each sample evaluated (in this case 32 sensor readings). The humidity of both the odor sample and the reference air sample used by the electronic nose to set a base line for resistance variations also has a substantial effect upon the sensor-array data. Hence, an estimate of the odor concentration can be considered to be an unknown function of 34 variables.

The conventional olfactometer used to obtain measurements of the eight samples was an eight-panelist station olfactometer used in accordance with the ASTM standard methods referred to above. Forty-four people randomly assigned to six panels on each of six days spread over a three week period. Other standard methods for selection of panelists, such as the CEN standard, could be used as well to obtain olfactometer measurements.

The data set resulting from the olfactometer and electronic nose measurements described above contained 480 cases, each case consisting of an odor concentration measurement obtained from the olfactometer, 32 sensor readings, and two humidity readings. Clearly, the goal is to find a method, that could be embodied in an apparatus, for processing 32 sensor readings and two humidity readings from a measurement of an odor of unknown concentration and providing as output a reasonably accurate estimate of the odor concentration that would be measured by a conventional (human panel) olfactometer.

One method that may be used to find a procedure for estimating a measurement (odor concentration in this case) that is possibly a non-linear function of many variables (34 here) is to use an artificial neural network. There are, however, many forms of artificial neural networks as well as alternative methods for performing non-linear regressions. The inventors selected a particular form of artificial neural network known as an Adaptive Logic Network (ALN) developed by one of the inventors, Dr. William W. Armstrong and sold by Dendronic Decisions Limited of Edmonton, Alberta, Canada. However, it is expected that other artificial neural networks could be used, as well as other non-linear regression techniques that are known to those who are skilled in the art, in the estimation of odor concentration from sensor array data.

ALN is a form of neurocomputing capable of modeling complex non-linear systems by using piece-wise linear surfaces. Basically, an unknown function (here odor concentration) is approximated by linear surfaces joined by fillets for smoothness. The ALN is described in detail at http://www.dendronic.com. A free demonstration version of software using ALN may be download from that website and was used in the embodiment of the invention used for testing the inventive method.

Conventionally, neutral networks are trained using raw data. In this case, the raw data appeared to be very noisy as some of the sensor responses did not appear to correlate at all with the odor concentration. As well, the large number of variables would reduce the accuracy of the training of the neural network.

The inventors determined that some preprocessing of the raw data was needed to reduce the number of variables and the noise. One well-known technique for doing so is principal component analysis, but other techniques such as cluster analysis could also be used. Those skilled in the art will be aware of other linear and non-linear techniques for reducing noise and dimensionality.

Principal component analysis is a well-known technique (see, for example: Chapter 11 of T. W. Anderson, An Introduction to Multivariate Statistical Analysis, John Wiley and Sons Inc., New York, London, 1958; George H. Dunteman, 1989. PRINCIPAL COMPONENT ANALYSIS, Sage Publication, ISBN 0803931042; and I. T. Jolliffe, 1985. PRINCIPAL COMPONENT ANALYSIS, Springer-Verlag New York, ISBN 0387962697) in which a space is linearly transformed into a new space such that the dimensionality of the new space is the same as the original space. In the transformation new variables are introduced that are uncorrelated with each other, but are linear combinations of all of the original variables (the 32 sensor readings and the two humidities). The degree to which each new variable contributes to the variance in the output variable (in this case the odor concentration measured by the olfactometer) is examined and may allow a drastic reduction in the number of variables used to train the neural network if most of the variance is only due to a few of the new variables. In this case, it was found that three of the new variables accounted for 98.9% of the variance in the odor concentration measurements by the olfactometer.

In effect, the result of the principal components analysis was that the odor concentration measurement could be treated as a function of three variables. Since the values of each of the three new variables for particular odor concentration measurement are known linear combinations of the 34 raw data values for that measurement, the problem was reduced to training a neural network using data sets each consisting of a odor concentration value measured by an olfactometer and three new variable values. The odor concentration is treated as the dependent variable (desired output) and the three new variables are treated as the independent variables (inputs).

Once a neural network is well-trained, it should output a reasonably good estimate of the odor concentration that an olfactometer would measure for an odor sample if the trained neural network is given a set of three new variable values calculated from a set of 34 raw data values obtained from the sample using the transformation determined by the principal components analysis of the test data set. Used on sample data not used to train or validate the neural network, odor concentration as measured by the olfactometer was calculated by the trained neural network with a mean absolute percentage error of 21.5%.

The testing of the inventive method and the apparatus is described in more detail in a paper entitled "Combining an Electronic Nose with an Artificial Neural Netwrok to Measure Odour Concentration" written by the inventors for presentation at the 1999 ASAE/CSAE-SCGR Annual International Meeting at Toronto, Ontario, Canada, Jul. 18–21, 1999, which is incorporated by reference in its entirety. Further details may be found in the Ph.D. thesis of the inventor Guoliang Qu in Bioresource Engineering submitted to the Department of Agricultural, Food and Nutritional Sciences, University of Alberta, Edmonton, Alberta, Fall, 1999, which is also incorporated by reference.

Once a neural network is well-trained for a particular sensor array and odor, the neural network may be used together with data processing to convert the raw sensor data and humidity readings into new variable values for input into the neural network to provide odor concentration measurements without the need for a human panel. The neural network and associated data processing may be added to the control system for a conventional electronic nose or may be an independent apparatus for interpreting data collected by electronic noses.

Figure 2:
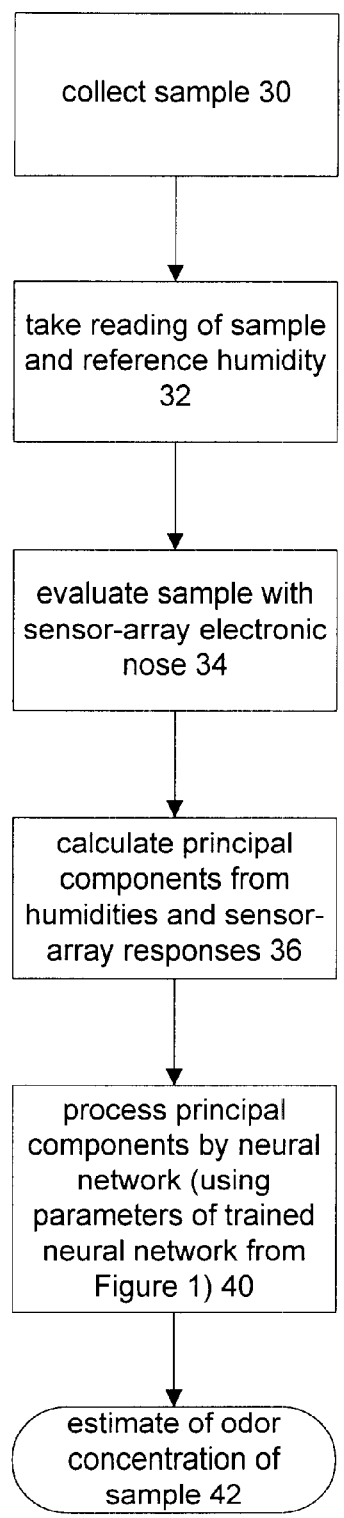
FIG. 2 is a schematic data flow diagram that illustrates the use of a neural network using parameters obtaining from the process illustrated in FIG. 1 to estimate odor concentration.
Figure 3:
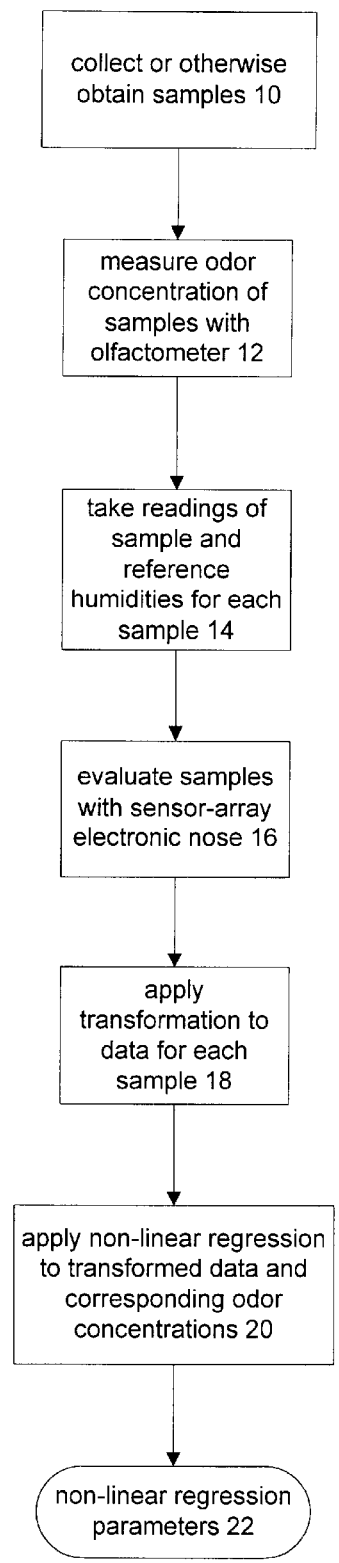
FIG. 3 is a schematic data flow diagram that illustrates the use of a linear transformation and non-linear regression to calibrate estimation of odor concentration.
Figure 4:
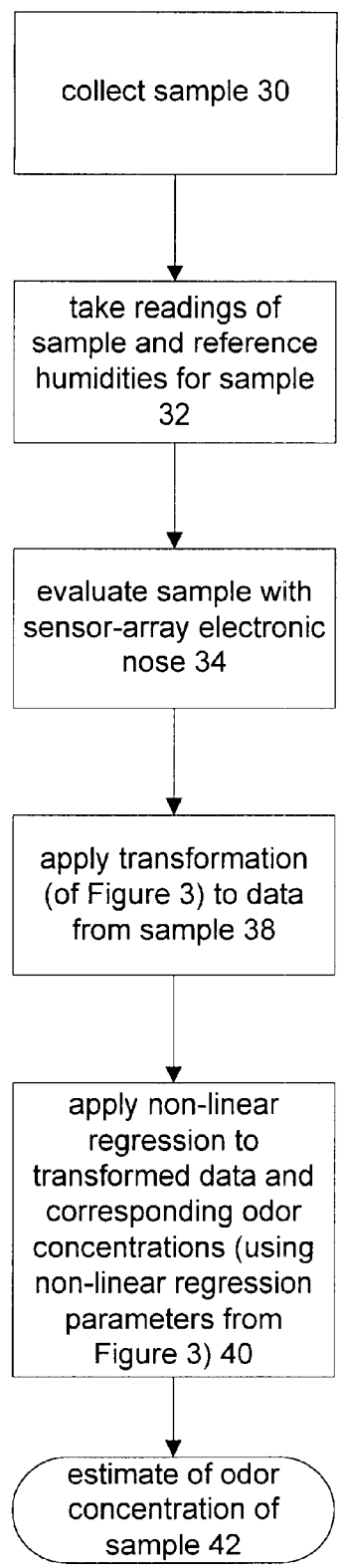
FIG. 4 is a schematic data flow diagram that illustrates the use of a linear transformation and non-linear regression to estimate odor concentration.

The inventive method and apparatus is illustrated generally in FIG. 1–4. FIGS. 1 and 2 illustrate the use of principal component analysis combined with a neural network. FIGS. 3 and 4 illustrate the inventive method more generally. In both cases, a sensor-array is calibrated using samples of air containing an odor that have also been measured for odor concentration using an olfactometer. FIGS. 1 and 3 illustrate the calibration method, while FIGS. 2 and 4 illustrate the estimation of the odor concentration using calibration data obtained using the methods illustrated in FIGS. 1 and 3, respectively.

In FIG. 1, air samples containing a particular odor are collected 10 or may be made up in a reproducible manner. The samples are measured 12 with an olfactometer, readings taken 14 of their humidity and the humidity of reference air used by the sensor array, and evaluated 16 by a sensor-array electronic nose. The resulting data sets are then processed 18 by principal components analysis to obtain the coefficients of a linear transformation that may be applied to a set the humidities and sensor readings to obtain the principal components of that set. The resulting sets of principal components of the data sets and the corresponding measured odor concentrations are then used to train 20 a neural network, resulting in a set of parameters 22 of the neural network.

In FIG. 2, a sample of air containing the particular odor used in the calibration process of FIG. 1, but of unknown concentration, is collected 30, readings taken 32 of the humidity of the sample and the reference air, the sample evaluated 34 using the sensor array, the principal components of the humidities and sensor readings data set calculated 36 using the linear transformation whose coefficients were calculated in the process illustrated in FIG. 1, and the principal components in turn processed 38 by a neural network set up using the parameters 22 to provide an estimate 40 of the odor concentration of the sample.

FIGS. 3 and 4 illustrate the same process as that illustrated in FIGS. 1 and 2, except that rather than processing the calibration data sets using principal components analysis, a more general transformation is indicated, and in rather than using a neural network, a more general non-linear regression is indicated. As discussed above, those skilled in the art with be aware of many transformations that may be used to reduce noise and dimensionality of the calibration data as well as non-linear regressions that may be applied to the transformed calibration data. As the steps of the process illustrated in FIGS. 3 and 4 correspond closely to those of FIGS. 1 and 2, the same reference numerals are used.

FIGS. 1–4 should be considered as illustrating both the steps of inventive method and embodiments of the inventive method in software to be added to the software used in conventional electronic noses and in hardware that may be added to conventional electronic noses. Hence the Figures should be considered be both flowcharts of software embodiments and block diagrams of systems (hardware). The invention may be embodied in a module to be added to a conventional electronic nose, in a separate device for use in analyzing data obtained from a conventional electronic nose, or in the form of software included in the software that controls a conventional electronic nose.

It is known, at least for conducting polymer sensor arrays, that the pattern of response of the array elements may vary from array to array and that over a period of time the response pattern of a specific array may change due to aging. The calibration procedures illustrated in FIGS. 1 and 3 might suggest that olfactometer measurements (involving a human panel and many measurements) must be made each time the inventive method is used to calibrate a system for use with a particular sensor-array electronic nose and to periodically recalibrate the system for a particular electronic nose.

One way to deal with any lack of consistency in sensor arrays may be to calibrate systems embodying the invention for more than one electronic nose at the same time by exposing the sensor-arrays of all of the electronic noses to be calibrated to the same samples in the same calibration session and determining the relevant parameters for each system from the data from each electronic nose.

While use of an olfactometer in the manner described above using fresh samples from nature is feasible for recalibration, it may also be possible to reuse for later calibration and recalibration the set of air samples whose odor concentrations were measured by an olfactometer to initially calibrate a system for a particular sensor array. In that case, the procedures for obtaining the parameters for the neural network in FIG. 1 and the non-linear regression parameters in FIG. 3 would use odor concentration measurements of the samples taken at a previous time by an olfactometer.

Further, the use of olfactometers and collected samples may be reduced by the use of samples made up for each calibration session from standardized laboratory chemicals using a "recipe" that provides a standard odor sufficiently similar to the odor whose concentration is to be measured that use of a collected sample is not necessary.

Of course, in some applications the target odor may be a synthetic odor rather than a natural odor such as that from swine barns, so that the recipe is known and once a correlation between the dilution of odor obtained from the recipe and measurements made by an olfactometer is determined, no further use of the olfactometer may be needed as new samples of predicted odor concentration may be made up from the recipe for use in calibration of sensor arrays.

What is claimed is:

1. A method for obtaining an estimate of the concentration of an odor in an air sample from data obtained by evaluating the sample with a sensor-array type electronic nose, the method comprising:

processing a set of air sample data including sensor-array data obtained from evaluating the air sample with the sensor-array type electronic nose and measurements of the humidity of the air sample and clean reference air used by the electronic nose to reduce noise in the air sample data and to decrease the dimensionality of that set of data to a predetermined number of dimensions, thereby obtaining a set of the predetermined number of air sample components; and applying a non-linear transformation to the set of air sample components to obtain as output an estimate of the concentration of the odor in the air sample, the non-linear transformation using parameters obtained by:

using an olfactometer to obtain discrete measurements of odor concentration from each of a plurality of calibration samples of air containing the odor, using the sensor-array type electronic nose to obtain a discrete set of calibration data from each of the calibration samples, each set including sensor-array data and measurements of the humidity of the calibration sample and the clean reference air used by the electronic nose, processing each set of calibration data to reduce noise in the air sample data and to decrease the dimensionality of that set of data to a predetermined number of dimensions, thereby obtaining a discrete set of the predetermined number of calibration components, and applying a non-linear regression to the sets of calibration components as input data and the corresponding measured odor concentrations as expected output to obtain the parameters of a non-linear transformation.

2. The method defined in claim 1, wherein:

the non-linear transformation is applied by a neural network to the set of air sample components to obtain as output an estimate of the concentration of the odor in the air sample, the neural network using parameters obtained by training a neural network using the sets of calibration components as input data and the corresponding measured odor concentrations as expected output.

3. The method defined in claim 1, wherein:

the set of air sample data is processed by applying principal components analysis to obtain, as the predetermined number of components of that set of data, that number of the principal components, and the calibration components are obtained by processing each set of calibration data by applying principal components analysis.

4. The method defined in claim 3, wherein:

the non-linear transformation is applied by a neural network to the set of air sample components to obtain as output an estimate of the concentration of the odor in the air sample, the neural network using parameters obtained by training a neural network using the sets of calibration components as input data and the corresponding measured odor concentrations as expected output.

5. A system for obtaining an estimate of the concentration of an odor in an air sample from data obtained by evaluating the sample with a sensor-array type electronic nose, the system comprising:

a component for processing a set of air sample data including sensor-array data obtained from evaluating the air sample with the sensor-array type electronic nose and measurements of the humidity of the air sample and clean reference air used by the electronic nose to reduce noise in the air sample data and to decrease the dimensionality of that set of data to a predetermined number of dimensions, thereby obtaining a set of the predetermined number of air sample components; and a component for applying a non-linear transformation to the set of air sample components to obtain as output an estimate of the concentration of the odor in the air sample, the non-linear transformation using parameters obtained by:

using an olfactometer to obtain discrete measurements of odor concentration from each of a plurality of calibration samples of air containing the odor, using the sensor-array type electronic nose to obtain a discrete set of calibration data from each of the calibration samples, each set including sensor-array data and measurements of the humidity of the calibration sample and the clean reference air used by the electronic nose, processing each set of calibration data to reduce noise in the air sample data and to decrease the dimensionality of that set of data to a predetermined number of dimensions, thereby obtaining a discrete set of the predetermined number of calibration components, and applying a non-linear regression to the sets of calibration components as input data and the corresponding measured odor concentrations as expected output to obtain the parameters of a non-linear transformation.

6. The system defined in claim 5, wherein:

the non-linear transformation is applied by a neural network component to the set of air sample components to obtain as output an estimate of the concentration of the odor in the air sample, the neural network component using parameters obtained by training a neural network using the sets of calibration components as input data and the corresponding measured odor concentrations as expected output.

7. The system defined in claim 5, wherein:

the set of air sample data is processed by applying principal components analysis to obtain, as the predetermined number of components of that set of data, that number of the principal components, and the calibration components are obtained by processing each set of calibration data by applying principal components analysis.

8. A system for obtaining an estimate of the concentration of an odor in an air sample from data obtained by evaluating the sample with a sensor-array type electronic nose, the system comprising:

a processor component for applying principal components analysis to a set of air sample data including sensor-array data obtained from evaluating the air sample with the sensor-array type electronic nose and measurements of the humidity of the air sample and clean reference air used by the electronic nose to obtain a predetermined number of principal components of the air sample data; and a neural network component for processing the principal components obtained from the air sample to obtain as output an estimate of the concentration of the odor in the air sample, the neural network using parameters obtained by:

using an olfactometer to obtain discrete measurements of odor concentration from each of a plurality of calibration samples of air containing the odor, using the sensor-array type electronic nose to obtain a discrete set of calibration data from each of the calibration samples, each set including sensor-array data and measurements of the humidity of the calibration sample and the clean reference air used by the electronic nose, applying principal components analysis to each set of calibration data to obtain a discrete set of the predetermined number of principal components, and training a neural network using the sets of principal components as input data and the corresponding measured odor concentrations as expected output to obtain the parameters of a trained neural network.

* * * * *

UNITED STATES PATENT AND TRADEMARK OFFICE
CERTIFICATE OF CORRECTION

PATENT NO.    : 6,411,905 B1
DATED         : June 25, 2002
INVENTOR(S)   : Qu et al.

It is certified that error appears in the above-identified patent and that said Letters Patent is hereby corrected as shown below:

<u>Title page,</u>
Item [75], Inventors, -- Guoliang Qu; John R. Feddes, both of Edmonton; Richard N. Coleman, Vegreville; William W. Armstrong; Jerry J. Leonard, both of Edmonton, all of (CA) --

Signed and Sealed this

Twelfth Day of November, 2002

*Attest:*

*Attesting Officer*

JAMES E. ROGAN
*Director of the United States Patent and Trademark Office*